United States Patent
Soubelet et al.

(10) Patent No.: US 8,233,688 B2
(45) Date of Patent: Jul. 31, 2012

(54) METHOD OF DETECTION AND COMPENSATION FOR RESPIRATORY MOTION IN RADIOGRAPHY CARDIAC IMAGES SYNCHRONIZED WITH AN ELECTROCARDIOGRAM SIGNAL

(75) Inventors: Elisabeth Soubelet, Meudon (FR); Jean Lienard, Igny (FR); Laurence Gavit-Houdant, New York, NY (US); Regis Vaillant, Villebon sur Yvette (FR)

(73) Assignee: General Electric Company, Schenectady, NY (US)

( * ) Notice: Subject to any disclaimer, the term of this patent is extended or adjusted under 35 U.S.C. 154(b) by 1093 days.

(21) Appl. No.: 12/054,989

(22) Filed: Mar. 25, 2008

(65) Prior Publication Data
US 2008/0240536 A1 Oct. 2, 2008

(30) Foreign Application Priority Data

Mar. 27, 2007 (FR) .................... 07 54070

(51) Int. Cl.
*A61B 6/00* (2006.01)
*G06K 9/00* (2006.01)
(52) U.S. Cl. .............. 382/131; 382/154; 382/128
(58) Field of Classification Search ........... 382/128–133
See application file for complete search history.

(56) References Cited

U.S. PATENT DOCUMENTS

| | | | |
|---|---|---|---|
| 4,387,722 A | 6/1983 | Kearns | |
| 4,994,965 A | 2/1991 | Crawford et al. | |
| 5,271,055 A | 12/1993 | Hsieh et al. | |
| 5,287,276 A | 2/1994 | Crawford et al. | |
| 5,623,929 A * | 4/1997 | Weng | 600/455 |
| 6,501,981 B1 * | 12/2002 | Schweikard et al. | 600/427 |
| 6,633,775 B1 | 10/2003 | Bernard | |
| 6,937,696 B1 * | 8/2005 | Mostafavi | 378/95 |
| 7,295,692 B2 | 11/2007 | Nay et al. | |
| 2003/0099390 A1 * | 5/2003 | Zeng et al. | 382/131 |
| 2005/0288578 A1 | 12/2005 | Durlak | |
| 2006/0235295 A1 * | 10/2006 | Boese et al. | 600/428 |

(Continued)

FOREIGN PATENT DOCUMENTS

DE 10 2005 017 492 A1 10/2006

(Continued)

OTHER PUBLICATIONS

Bassem, Richard, Janier, and Croisille, "Cardiac and Respiratory Self-Gated Cine MRI in the Mouse at 7T," Magnetic Resonance in Medicine, 2006.

(Continued)

*Primary Examiner* — Jack Berman
*Assistant Examiner* — David E Smith
(74) *Attorney, Agent, or Firm* — Global Patent Operation; Jonathan E. Thomas

(57) ABSTRACT

A method of detection and compensation for respiratory motion improves the registration between a 3D pre-operation image and X-ray images acquired during a cardiac intervention. By synchronizing the X-ray images with the electrocardiogram, the disclosed method thus eliminates the motion related to the heart cycle from these images, thus isolating the contribution of the respiratory motion. From this point, an algorithm is proposed capable of attributing the motion remaining in the radiography images to respiration. The algorithm also enables this motion to be detected and compensated for in order to obtain a registration between 3D cardiac images and radiography images.

11 Claims, 1 Drawing Sheet

U.S. PATENT DOCUMENTS

2007/0238947 A1* 10/2007 Pescatore et al. .............. 600/407
2008/0147086 A1* 6/2008 Pfister et al. .................. 606/130
2008/0226149 A1* 9/2008 Wischmann et al. ......... 382/131

FOREIGN PATENT DOCUMENTS

| FR | 2 848 093 | 12/2002 |
| FR | 2 847 798 | 6/2003 |
| WO | WO 03/096894 A1 | 11/2003 |

OTHER PUBLICATIONS

John N. Amoore and John P. Ridgway, "A System for Cardiac and Respiratory Gating of a Magnetic Resonance Imager," Clin. Phys. Physiol. Meas., 1989, vol. 10, No. 3, 283-286, Department of Medical Physics and Medical Engineering, Royal Infirmary, Edinburgh EH3 9YW, UK.

* cited by examiner

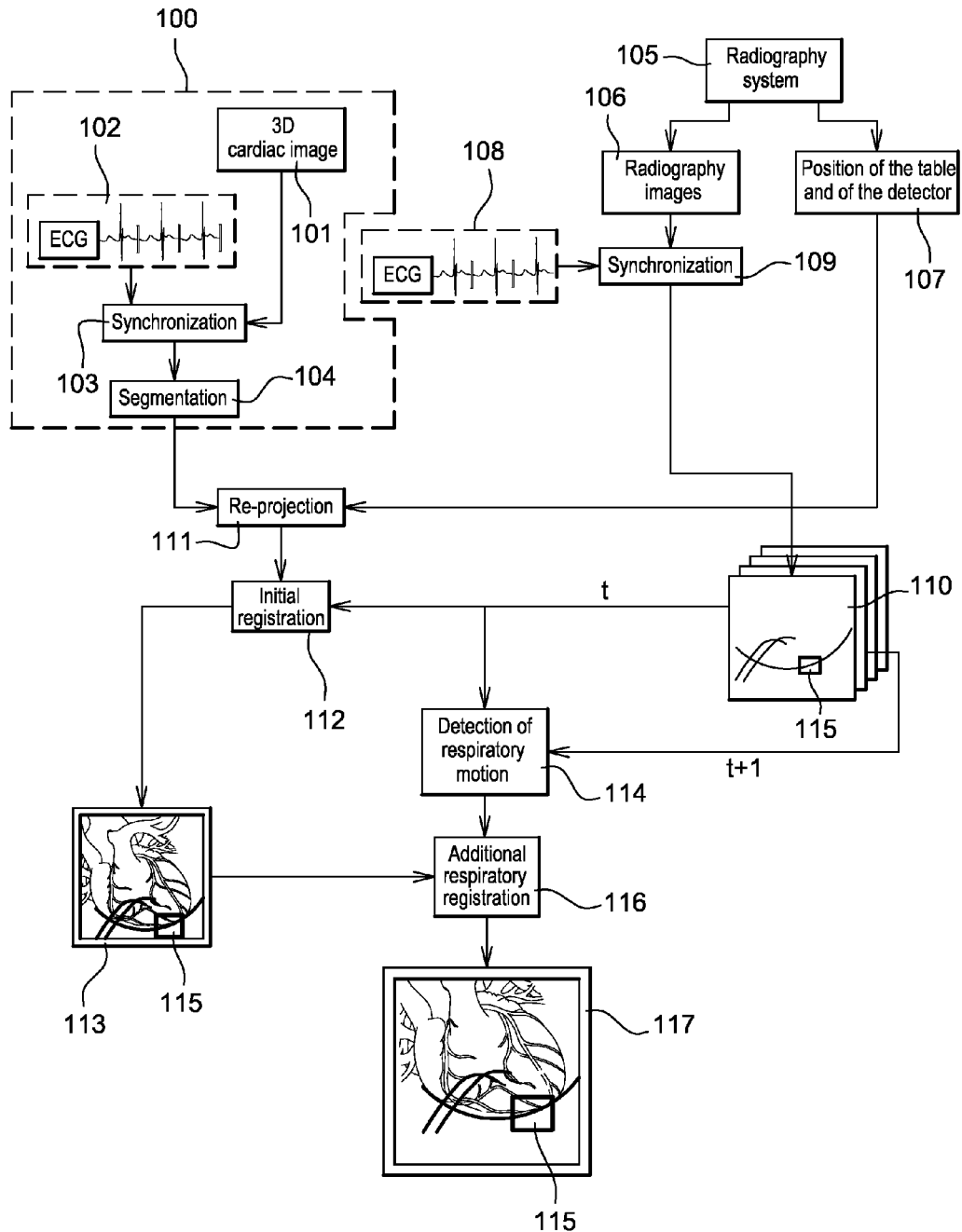

METHOD OF DETECTION AND COMPENSATION FOR RESPIRATORY MOTION IN RADIOGRAPHY CARDIAC IMAGES SYNCHRONIZED WITH AN ELECTROCARDIOGRAM SIGNAL

CROSS-REFERENCE TO RELATED APPLICATIONS

This application claims the right of priority, under 35 USC 119(a)-(d), to the earlier filing date of co-pending French patent application serial number 0754070, filed 27 Mar. 2007, which is herein incorporated by reference in its entirety. The basis for this claim of right of priority is France's membership in the World Trade Organization.

BACKGROUND

1. Field of the Invention

Embodiments of the present invention find particularly advantageous but not exclusive application in the field of medical imaging, and more particularly in the field of X-ray imaging in cardiology.

2. Prior Art

X-ray imaging is now widely used for the diagnosis and processing of cardiac pathologies. The treatment may include coronaroplasty, valve replacement, electrophysiology etc.

In a certain number of interventional procedures, the practitioner must pass catheters and/or guides into vessels or cavities of the heart. These interventions enable different procedures such as embolization, dilation, desobstruction, placing of stents, and ablation. These techniques make it possible to avoid heavy surgical intervention.

During the interventional procedure, the operator guides the operating tool chiefly by means of radiography images. However, anatomical structures of strategic importance, such as the left ventricle and the pulmonary veins in the case of an interventional procedure for ablation of auricular fibrillation, and the coronary sinus and its branches in the case of biventricular stimulation procedure for example, are not depicted by X-ray systems because they show no contrast with the surrounding anatomical structures.

For all these applications, knowledge of anatomical information would be very useful during the operation to locate the tools or catheters relative to these structures.

There are many classic solutions used to make these anatomical structures visible in the radiography image. A first classic solution uses a contrast agent. This contrast agent is generally an iodized compound. However, this type of solution has drawbacks, for iodized compounds are often sources of allergies in the patient and are also toxic for the kidneys.

Another more recent approach consists of the production of a 3D image at the beginning of the operation or before the operation, using computerized tomography or magnetic resonance or by rotation of the X-ray system. This approach comprises means capable of resetting the pre-operative 3D images with projection images of the radiography system, for their subsequent fusion. This fusion enables the practitioner to view the operating tool and the anatomy at the same time. This type of approach is widely dealt with in the prior art.

However, this type of approach has drawbacks. Indeed, the main problem encountered in the specific part of the anatomy, namely the heart, is that it undergoes a high degree of motion due to the patient's heart cycle and respiration. Today, 3D computerized tomography images obtained before the operation may be synchronized with electrocardiograms, enabling the reconstruction of the heart at a specific phase of the cardiac cycle and hence the elimination of cardiac motion. Similarly, since the scanner acquisition is brief, the patient can reasonably be expected to hold his breath during the acquisition, thus eliminating the problem of respiratory motion.

Unlike pre-operation images, radiography images are dynamic and contain both heart motions and respiratory motions. Heart motion is a complex motion consisting of translation, rotation and deformation. If the registration between the pre-operation image and the X-ray image is constrained to a rigid registration, then only the radiography images acquired at the same phase of the heart cycle as the pre-operation images are used. This enables the elimination of the cardiac motion of the X-ray images. However, the respiratory motion is always present in X-ray images, and therefore does not enable precise registration with the pre-operation images.

SUMMARY OF THE INVENTION

Embodiments of the invention aim at overcoming the drawbacks of the above-mentioned techniques. To this end, the invention proposes a method for detecting and compensating for respiratory motion in radiography cardiac images synchronized with an electrocardiogram signal.

The embodiments of the present invention include an imaging system designed for use in a medical intervention procedure. The imaging system comprises a first system of acquisition of images of a first mode, using a catheter in an anatomical region of the patient and configured to produce a first image of the anatomical region. The imaging system comprises a second system of image acquisition in a second mode, configured to produce a 3D model of the anatomical region.

An embodiment of the invention comprises an algorithm capable of determining an anatomical reference system common to both image acquisition systems. The algorithm of the invention is configured to process executable instructions to register the 3D model with the radiography image, in response to the common reference system. The registration thus obtained can be adjusted manually by a user.

At present, in cardiology image formation, increasing numbers of images are being synchronized with an electrocardiogram. Consequently, it is important to have a means of computing the respiration so that the motion of the heart in the image is perfectly known at least between two cycles of the heart.

To this end, the algorithm of the invention synchronizes the radiography images with the electrocardiogram signal in order to separate the motion due to the cardiac cycle from this image. From this point onwards, the motion that remains in the radiography images can be attributed to the respiration which can be detected and compensated for in order to obtain registration between the 3D cardiac images and the radiography images.

Of all the acquired and synchronized radiography images, the algorithm of the invention selects only those acquired in the same phase of the cardiac cycle as the 3D cardiac images.

The 3D cardiac image is segmented in order to take only that part of the anatomy that must be fused with the radiography images. The algorithm of the invention carries out an initial registration between one of the selected radiography images and the segmented 3D cardiac image. Then, an algorithm for detecting the respiratory motion is applied to the images that are synchronized and have undergone the initial registration.

Respiratory motion is fairly simple. As an initial approximation, the respiratory motion may be considered to be a rigid motion without deformation of the heart. It may even be considered to be an essentially translational motion. It is therefore theoretically possible to calculate this motion and compensate for it in order to obtain efficient registration with 3D cardiac images acquired at a given phase of the cardiac cycle. As a second approximation, the respiratory motion may be considered to be a more complex motion with a deformation of the heart. This is implemented by a finer modeling of respiratory motion.

Then, the algorithm performs an additional registration between the 3D cardiac image and the synchronized radiography images in compensating for the respiration by the combination of the initial registration and of the detected respiratory motion.

The invention is thus particularly suited to an ablation operation procedure in which the ablation catheter is used to "burn" the tissue of the cardiac wall in order to modify electrical conduction on its surface. Indeed, through an initial registration and then an additional registration, the 3D cardiac images are put into in a state of concordance with the projection images of the fluoroscopy system. As a consequence, pulmonary veins in other regions involved in the launching and tracking of an auricular fibrillation may be identified with greater precision and simplicity in the radiography images, thus improving the success rate of a catheter ablation procedure.

The embodiments of the invention presented here also constitute a system and method by which 3D images of anatomical structures, for example the coronary sinus and the left ventricle, may be put into concordance with projection images of the radiography system, thus enabling the navigation and positioning of the stimulation electrodes at the place most suited in the case of biventricular stimulation procedures.

The fact of having perfect concordance between the two images enables, for example, a cardiologist to carry out the real-time tracking of the progress of a vascular tool during an operation or again the tracking of catheters whenever they may be.

Embodiments of the invention thus enable registration with greatly reduced tracking time as compared with the prior art.

More specifically, an embodiment of the invention provides a method for detecting and compensating for respiratory motion, wherein:

a 3D image is produced of a patient's heart by means of a 3D imaging system, an electrocardiogram is recorded at the same time as the 3D image is acquired, a segmentation of the 3D image is performed, the patient's heart is exposed to radiation produced by a radiography imaging system, through a detector, a succession of radiography images representing an internal structure of the heart is obtained, wherein the succession of acquired radiography images is synchronized with the electrocardiogram, an initial registration is computed between one of the radiography images and a re-projection of the 3D image, at least one part of the radiography images is analyzed in order to highlight a respiratory motion therein, an additional respiratory registration linked to the respiration is determined, a fusion is made of the re-projected 3D image with radiography images in compensating for the respiratory motion of the radiography images with the additional registration, the fusion image is displayed on a viewing screen Embodiments of the invention also relate to an X-ray apparatus for the implementation of said method for detecting and compensating for respiratory motion in radiographic cardiac images synchronized with an electrocardiogram signal.

BRIEF DESCRIPTION OF THE DRAWINGS

Embodiments of the invention will be understood more clearly from the following description and the single accompanying figure. This figure is given by way of an indication and in no way restricts the scope of the invention.

FIG. 1 illustrates means implementing the method of the invention.

DETAILED DESCRIPTION OF EMBODIMENTS OF THE INVENTION

FIG. 1 illustrates means implementing the method for detecting respiratory motion in a cardiac image. The example of FIG. 1 can be used in a medical intervention procedure such as for example a procedure for the ablation of auricular fibrillation or a biventricular procedure.

In the example of FIG. 1, the X-ray apparatus (not shown) comprises both a 3D imaging system and a radiography imaging system. The radiography imaging system may be distinct or it may be included in the 3D imaging system.

The respiratory motion detection algorithm of the invention is implemented by a processor (not shown) of the X-ray apparatus.

The 3D imaging system may be, inter alia, a computerized tomography machine, a radiography system taking 3D images by rotation, magnetic resonance systems, positron-emission tomography (PET), ultrasonic systems, nuclear medicine systems and 3D radiography systems.

Before or during a medical intervention, the phase 100 is performed. This phase 100 consists in acquiring a 3D image synchronized with an electrocardiogram. This phase 100 comprises the step 101 to the step 104. At the step 101, the 3D imaging system acquires the digital volume of the desired part of the anatomy which in this case is a patient's heart.

In the step 102, simultaneously with the acquisition of the 3D images, an electrocardiogram signal (ECG) is acquired in order to obtain a 3D reconstruction synchronized with the ECG.

At the step 103, in a preferred embodiment, synchronization is performed between the computerized tomography data and the ECG data. The synchronization is done for one or more phases of the cardiac cycle. In another embodiment, the computerized tomography data are not synchronized with the ECG data. In this case, the 3D image is obtained for example by an average of the 3D image for all the phases of the cardiac cycle.

At the step 104, a segmentation of the digital volume which may or may not be synchronized with the ECG is performed. However, the synchronized reconstruction of the ECG, followed by a reconstruction by segmentation of the digital volume at a phase of the cardiac cycle, enables motion-free imaging of the heart.

Starting with the step 105, all the following actions are performed during the medical intervention phase. In the step 106, the radiography system of the step 105 acquires a succession of radiography images. In a preferred embodiment, these radiography images are fluoroscopy images.

The radiography system of the step 105 also enables the definition, in the step 107, of a reference system common to both imaging systems. To this end, an existing algorithm is performed for determining an acquisition geometry of a radiography imaging system as a function of parameters of the system. The acquisition geometry of the system is relative to a positioning of the tube (not shown) and of the detector (not shown) in the given reference system. This acquisition geometry is defined both by the position in space of a pillar (of the X-ray apparatus and that of an examination table (not shown) on which the patient reclines, relative to a given reference system.

The fact of defining this common reference system enables a reference link to be set up between the 3D imaging system and the radiography imaging system. This enables the interlinking of items of geometrical information that are known and belong to each image acquisition system.

In the step 108, simultaneously with the acquisition of the radiography images, an electrocardiogram (ECG) signal is acquired. At the step 109, a synchronization is performed between the radioscopy image data and the ECG data. This synchronization is used to determine the set of synchronized radiography images 110 acquired at the same cardiac cycle phase. If the 3D image is also synchronized with the ECG, the same cardiac phase is chosen for both acquisitions. The radiography images 110 are segmented in order to separate the objects from one another and from the background in the image in extracting the contours or in segmenting the image into homogenous regions.

At the step 111, the 3D image is re-projected in order to obtain a projected image of the 3D image along the same orientation as the radiography imaging system. This orientation is given by the reference system of the step 107.

At the step 112, an initial preferably automatic registration, of the re-projected digital volume with one of the radiography images 110, in synchronization with the cardiac motion, is computed. This initial registration may be done or adjusted manually by user. This initial registration is redone or recomputed whenever the system or the patient is in motion.

The registration may be implemented by several existing methods, especially:
the superimposition of a catheter visible in the radiography images with anatomical structures visible in the 3D model,
the putting of the external contours of the anatomical structures into a state of concordance,
the search for visible vessels that are identical in the volume with vessels that are opacified during the radiography acquisition.

The result of the initial registration is a fusion image 113 of the re-projected digital volume with, for example, the radiography image 110 obtained at the instant t.

At the step 114, an algorithm is applied for detecting respiratory motions between the radiography image 110 obtained at the instant t and the following radiography image 110 obtained at the instant t+i. Thus algorithm is intended for the detection of a shift of components common to these two images. This shift is due to the patient's respiratory motion, in considering naturally that neither the system nor the patient is in motion.

The shift of the components in the radiography images 110 is slower because there is no longer any motion present except the respiratory motion. Consequently, it is enough to detect a component of the image and track the shift of this component to detect the respiratory motion.

The algorithm for detecting motion in an image may be, inter alia, an algorithm for correlation in the whole image, an algorithm for detecting identified elements having high contrast or any other type of existing algorithm.

In one example of detection, the catheter of the coronary sinus whose characteristic shape is clearly visible in the radiography image is chosen. Consequently, the common component is chosen as one belonging to this catheter. Thus, the same component 115 belonging to said catheter is selected both in the radiography image obtained at the incident t corresponding to the radiography images used during the initial registration and in the next radiography image 110 obtained at the instant t+i. The result of the comparison between the coordinates of the component 115 in these two images constitutes the patient's respiratory motion. And the sign of this result provides information on the sense of shift of the motion.

At the step 116, an additional registration is computed by combining the initial registration and the respiratory motion detected at the step 114. The additional respiratory registration is applied between the re-projected digital volume and the radiography image 110 obtained at the instant t+i, as a function of the respiratory motion detected at the step 114. This enables the performance of a registration complementary to the initial registration in order to compensate for the respiratory motion.

The additional registration enables the shifting of the re-projected digital volume as a function of the shifting of the respiratory motion. The re-projected digital volume is thus shifted to follow the radiography image 110. This leads to a situation where the anatomical structures of the digital volume are always at the right place relative to the radiography image 110.

The additional registration outputs a second fusion image 117 of the re-projected digital volume with the selected radiography image 110. The second fusion image 117 is viewed on the viewing screen.

What is claimed is:

1. A method for detecting and compensating for respiratory motion, the method comprising:
producing a 3D image of a patient's heart by means of a 3D imaging system;
recording an electrocardiogram at the same time as the 3D image is acquired;
performing a segmentation of the 3D image;
exposing the patient's heart to radiation produced by a radiography imaging system;
obtaining, through a detector, a succession of radiography images representing an internal structure of the heart;
synchronizing the succession of acquired radiography images with the electrocardiogram;
computing an initial registration between one of the radiography images and a re-projection of the 3D image;
analyzing at least one part of the radiography images wherein the analysis is synchronized in order to highlight a respiratory motion therein, the analyzing step comprising:
selecting a component of an identifiable object common to the synchronized radiography image obtained at an instant t and the synchronized radiography image obtained at an instant t+1;
computing Cartesian coordinates of this component both in the synchronized radiography image obtained at the instant t and the synchronized radiography image obtained at the instant t+1; and
comparing the computed coordinates, wherein the result of this comparison constitutes the respiratory motion and a sign of the result of the comparison provides information on the sense of the shift of the motion;

determining an additional respiratory registration linked to the respiration;

making a fusion of the re-projected 3D image with radiography images in compensating for the respiratory motion of the radiography images with the additional registration; and displaying the fusion image on a viewing screen.

2. A method according to claim 1, further comprising:

synchronizing the 3-D image with the electrocardiogram; and making a selection, from among the set of synchronized radiography images, of those images acquired in the same phase of the cardiac cycle as the digital volume to perform the registration and detection of the respiratory motion.

3. A method according to claim 1, further comprising:

taking an average of the 3D image on all the phases of the cardiac cycle.

4. A method according to claim 1, wherein the re-projection of the 3D image comprises:

determining a reference system common to the 3D imaging system and to the radiography imaging system;

determining an orientation of the radiography imaging system as a function of the common reference system; and re-projecting the 3D image according to the orientation of the radiography imaging system.

5. A method according to claim 1, wherein the initial registration is done or adjusted manually.

6. A method according to claim 1, wherein the initial registration is recomputed or redone manually whenever the imaging system or the patient is in motion.

7. A method according to claim 1, wherein the computation of the additional registration comprises:

combining the initial registration with the respiratory motion.

8. A method according to claim 1, wherein during the additional respiratory registration, the re-projected 3D image is shifted as a function of the respiratory motion.

9. A method according to claim 1, wherein the 3D image is acquired before the medical intervention with a 3-D imaging system distinct from the radiography imaging system.

10. A method according to claim 1, wherein the 3D image is acquired at the beginning of the medical intervention with a 3D imaging system comprising the radiography imaging system.

11. X-Ray apparatus for the implementation of a method of detection and compensation for respiratory motion in radiography cardiac images synchronized with an electrocardiogram signal according to claim 1.

* * * * *